United States Patent
Gustafsson et al.

(10) Patent No.: US 6,413,769 B1
(45) Date of Patent: *Jul. 2, 2002

(54) α(1,3) GALACTOSYLTRANSFERASE NEGATIVE PORCINE CELLS

(75) Inventors: Kenth T. Gustafsson, Buckinghamshire (GB); David H. Sachs, Newton; Manfred W. Baetscher, Winchester, both of MA (US)

(73) Assignees: University of London, London (GB); The General Hospital Corporation, Boston, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/929,940

(22) Filed: Sep. 15, 1997

Related U.S. Application Data

(63) Continuation of application No. 08/716,443, filed as application No. PCT/US95/03940 on Mar. 31, 1995, now abandoned, which is a continuation-in-part of application No. 08/228,933, filed on Apr. 13, 1994, now abandoned.

(51) Int. Cl.[7] ............... C12N 5/00; C12N 15/00; A61K 48/00
(52) U.S. Cl. ............... 435/325; 435/320.1; 435/455; 424/93.21
(58) Field of Search .................. 800/8, 13, 14, 800/17, 25; 435/325, 455, 320.1; 424/93.21

(56) References Cited

U.S. PATENT DOCUMENTS 5,821,117 A  * 10/1998 Sandrin et al.

OTHER PUBLICATIONS

Mullins et al (1996) Journal of Clinical Investigation 98, pp. S37–S40.*
Seamark (1994) Reproductive Fertility and Development 6, 653–657.*
Bradley et al. (1992) Bio/Technol. 10, 534–539.*
Mullins et al. (1996) J. Clin. Invest. 98, S37–S40.*
Shim et al. (1997) Biol. Reprod. 57, 1089–1095.*
Vanhove et al. (1998) Annals N.Y. Acad. Sci. 862, 28–36.*
Fassler et al. (1995) Int. Arch. Allergy Immunol. 106, 323–334.*
Morrow et al. (1993) Curr. Op.Biotech. 4, 577–582.*
Kim et al. (1978) J. Animal Sci. 46, 1648–1657.*
Seamark et al. (1994) Reprod. Fert. Devel. 6, 653–657.*

* cited by examiner

*Primary Examiner*—Deborah Crouch
(74) *Attorney, Agent, or Firm*—Elliot M. Olstein; Raymond J. Lillie

(57) ABSTRACT

Transgenic swine in which the normal expression of α(1, 3) galactosyltransferase is prevented in at least one organ of tissue type. The absence or inactivation of this enzyme prevents the production of carbohydrate moieties having the distinctive terminal Galα1-3Galβ1-4GlcNAc epitope that is a significant factor in xenogeneic, particularly human, transplant rejection of swine grafts.

4 Claims, 6 Drawing Sheets

FIG. 1A

Figure 4:
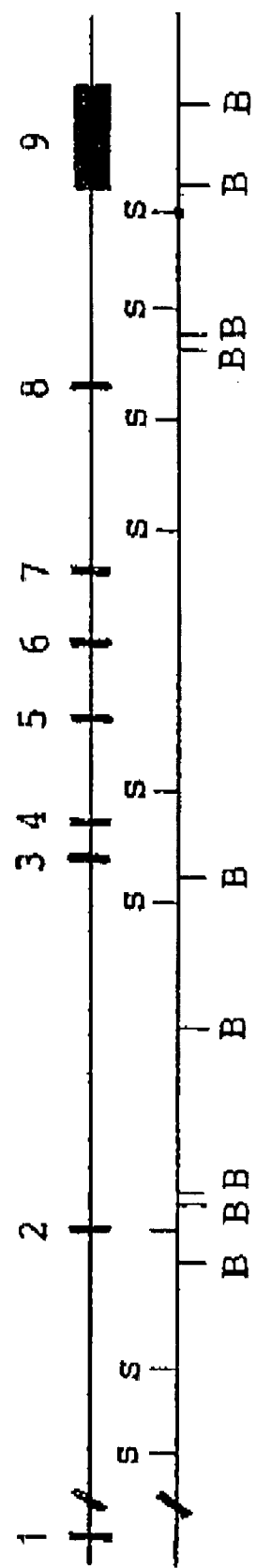

5'-CATGAGGAGA AAATA ATG AAT GTC AAA GGA AGA GTG GTT CTG TCA
ATG CTG CTT GTC TCA ACT GTA ATG GTT TGG GAA TAC ATC
AAC AGC CCA GAA GGT TCT TTG TTC TGG ATA TAC CAG TCA AAA AAC
CCA GAA GTT GGC AGC AGT GCT CAG AGG GGC TGG TTT CCG AGC
TGG TTT AAC AAT GGG ACT CAC AGT TAC CAC GAA GAA GAA GAC GCT
ATA GGC AAC GAA AAG GAA CAA CAA AGA GAA AAC AGA GGA GAG
CTT CCG CTA GTG GAC TGG TTT AAT CCT GAG AAA CGC CCA GAG GTC
GTG ACC ATA ACC AGA TGG AAG GCT CCA GTG GTA TGG GAA GGC ACT
TAC AAC AGA GCC GTC TTA GAT AAT TAT TAT GCC AAA CAG AAA ATT
ACC GTG GGC TTG ACG GTT TTT GCT GTC GGA AGA TAC ATT GAG CAT
TAC TTG GAG GAG TTC TTA TTA TCT GCA AAT ACA TAC TTC ATG GTT
GGC CAC AAA GTC ATC TTT TAC ATC ATG GTG GAT ATC TCC AGG
ATG CCT TTG ATA GAG CTG GGT CCT CTG CGT TCC TTT AAA GTG TTT
GAG ATC AAG TCC GAG AAG AGG TGG CAA GAC ATC GAC ATG ATG CGC

Match with FIG 1b

FIG. 1B

Match with FIG. 1a

ATG AAG ACC ATC GGG GAG CAC ATC CTG GCC CAC ATC CAG CAC GAG
GTG GAC TTC CTC TGC ATG GAC GTG GAT CAG GTC TTC CAA AAC
AAC TTT GGG GTG GAG ACC CTG GGC CAG TCG GTG GCT CAG CTA CAG
GCC TGG TGG TAC AAG GCA CAT CCT GAC GAG TTC ACC TAC GAG AGG
CGG AAG GAG TCC GCA GCC TAC ATT CCG TTT GGC CAG GGG GAT TTT
TAT TAC CAC GCA GCC ATT TTT GGG GGA ACA CCC ACT CAG GTT CTA
AAC ATC ACT CAG GAG TGC TTC AAG GGA ATC CTC CAG GAC AAG GAA
AAT GAC ATA GAA GCC GAG TGG CAT GAT GAA AGC CAT CTA AAC AAG
TAT TTC CTT CTC AAC AAA CCC ACT AAA ATC TTA TCC CCA GAA TAC
TGC TGG GAT TAT CAT ATA GGC ATG TCT GTG GAT ATT AGG ATT GTC
AAG ATA GCT TGG CAG AAA AAA GAG TAT AAT TTG GTT AGA AAT AAC
ATC TGA CTTTAAATTG TGCCAGCAGT TTTCTGAATT TGAAAGAGTA
TTACTCTGGC TACTTCCTCA GAGAAGTAGC ACTTAATTTT AACTTTAAA
AAAATACTAA CAAAATACCA ACACAGTAAG TACATATTAT TCTTCCTT -3'

FIG. 2A

| | | | | | |
|---|---|---|---|---|---|
| Porcine | MNVKGRVVLS | MLLVSTVMVV | FWEYINSPEG | SLFWIYQSKN | PEV-GSSAQR49 |
| Bovine | MNVKGKVILS | MLVVSTVIVV | FWEYIHSPEG | SLFWINPSRN | PEVGGSSIQK50 |
| Murine | MNVKGKVILL | MLIVSTVVVV | FWEYVNSPDG | SFLWIYHTKI | PEVGENRWQK50 |
| | | | | | |
| Porcine | GWWFPSWFNN | GTHSYHEEED | AIGNEKEQRK | EDNRGELPLV | DWFNPEKRPE99 |
| Bovine | GWWLPRWFNN | GYH---EEDG | DINEEKEQRN | EDESK-LKLS | DWFNPFKRPE96 |
| Murine | DWWFPSWFKN | GTHSYQ-EDN | VEGRREKGRN | GDRIEEPQLW | DWFNPKNRPD99 |
| | | | | | |
| Porcine | VVTITRWKAP | VVWEGTYNRA | VLDNYYAKQK | ITVGLTVFAV | GRYIEHYLEE149 |
| Bovine | VVTMTKWKAP | VVWEGTYNRA | VLDNYYAKQK | ITVGLTVFAV | GRYIEHYLEE146 |
| Murine | VLTVTPWKAP | IVWEGTYDTA | LLEKYYATQK | LTVGLTVFAV | GKYIEHYLED149 |
| | | | | | |
| Porcine | FLISANTYFM | VGHKVIFYIM | VDDISRMPLI | ELGPLRSFKV | FEIKSEKRWQ199 |
| Bovine | FLTSANKHFM | VGHPVIFYIM | VDDVSRMPLI | ELGPLRSFKV | FKIKPEKRWQ196 |
| Murine | FLESADMYFM | VGHRVIFYVM | IDDTSRMPVV | HLNPLHSLQV | FEIRSEKRWQ199 |

Match with FIG 2b

FIG. 2B

Match with FIG. 2a

```
Porcine   DISMMRMKTI GEHILAHIQH EVDFLFCMDV DQVFQNNPGV ETLGQSVAQL 249
Bovine    DISMMRMKTI GEHIVAHIQH EVDFLFCMDV DQVFQDKFGV ETLGESVAQL 246
Murine    DISMMRMKTI GEHILAHIQH EVDFLFCMDV DQVFQDNFGV ETLGQLVAQL 249

Porcine   QAWWYKAHPD EFTYERRKES AAYIPFGQGD FYYHAAIFGG TPTQVLNITQ 299
Bovine    QAWWYKADPN DFTYERRKES AAYIPFGEGD FYYHAAIFGG TPTQVLNITQ 296
Murine    QAWWYKASPE KFTYERRELS AAYIPFGEGD FYYHAAIFGG TPTHILNLTR 299

Porcine   ECFKGILQDK ENDIEAEWHD ESHLNKYFLL NKPTKILSPE YCWDYHIGMS 349
Bovine    ECFKGILKDK KNDIEAQWHD ESHLNKYFLL NKPTKILSPE YCWDYHIGLP 346
Murine    ECFKGILQDK KHDIEAQWHD ESHLNKYFLF NKPTKILSPE YCWDYQIGLP 349

Porcine   VDIRIVKIAW QKKEYNLVRN NI 371
Bovine    ADIKLVKMSW QTKEYNVVRN NV 368
Murine    SDIKSVKVAW QTKEYNLVRN NV 371
```

FIG. 3
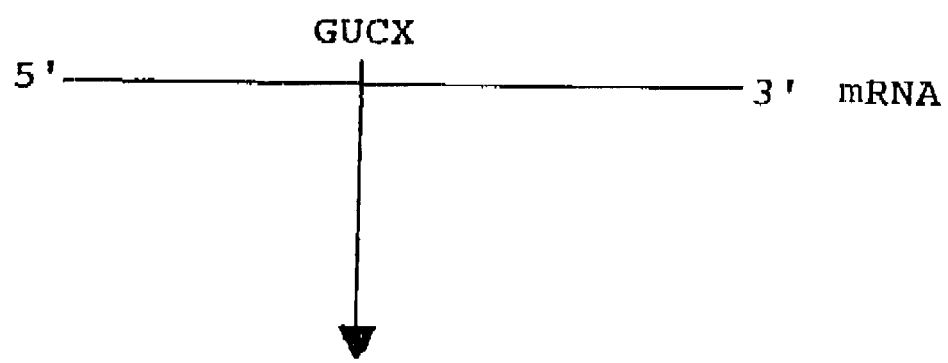
consensus ribozyme cleavage site
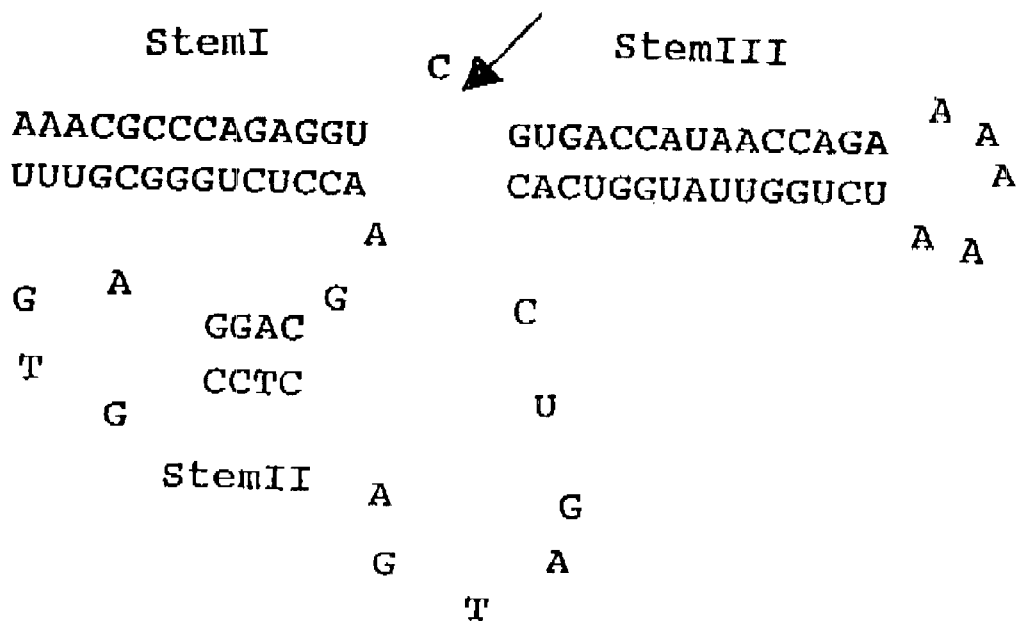

Genomic Organization of the Mouse
α(1,3) Galactosyltransferase Gene

SEQUENCE LISTING (1) GENERAL INFORMATION:

(iii) NUMBER OF SEQUENCES:26

(2) INFORMATION FOR SEQ ID NO:1:

(i) SEQUENCE CHARACTERISTICS:
        (A) LENGTH: 1269 bases
        (B) TYPE:nucleic acid
        (C) STRANDEDNESS:single
        (D) TOPOLOGY:linear (iii) HYPOTHETICAL:NO (iv) ANTI-SENSE:NO (xi) SEQUENCE DESCRIPTION:SEQ ID NO:  1:

```
CATGAGGAGA AAATA ATG AAT GTC AAA GGA AGA GTG GTT CTG TCA ATG              48
                 Met Asn Val Lys Gly Arg Val Val Leu Ser Met
                  1               5                      10

CTG CTT GTC TCA ACT GTA ATG GTT GTG TTT TGG GAA TAC ATC AAC AGC           96
Leu Leu Val Ser Thr Val Met Val Val Phe Trp Glu Tyr Ile Asn Ser
             15                  20                  25

CCA GAA GGT TCT TTG TTC TGG ATA TAC CAG TCA AAA AAC CCA GAA GTT          144
Pro Glu Gly Ser Leu Phe Trp Ile Tyr Gln Ser Lys Asn Pro Glu Val
         30                  35                  40

GGC AGC AGT GCT CAG AGG GGC TGG TGG TTT CCG AGC TGG TTT AAC AAT          192
Gly Ser Ser Ala Gln Arg Gly Trp Trp Phe Pro Ser Trp Phe Asn Asn
     45                  50                  55

GGG ACT CAC AGT TAC CAC GAA GAA GAA GAC GCT ATA GGC AAC GAA AAG          240
Gly Thr His Ser Tyr His Glu Glu Glu Asp Ala Ile Gly Asn Glu Lys
 60                  65                  70                  75

GAA CAA AGA AAA GAA GAC AAC AGA GGA GAG CTT CCG CTA GTG GAC TGG          288
Glu Gln Arg Lys Glu Asp Asn Arg Gly Glu Leu Pro Leu Val Asp Trp
                 80                  85                  90

TTT AAT CCT GAG AAA CGC CCA GAG GTC GTG ACC ATA ACC AGA TGG AAG          336
Phe Asn Pro Glu Lys Arg Pro Glu Val Val Thr Ile Thr Arg Trp Lys
             95                 100                 105

GCT CCA GTG GTA TGG GAA GGC ACT TAC AAC AGA GCC GTC TTA GAT AAT          384
Ala Pro Val Val Trp Glu Gly Thr Tyr Asn Arg Ala Val Leu Asp Asn
        110                 115                 120

TAT TAT GCC AAA CAG AAA ATT ACC GTG GGC TTG ACG GTT TTT GCT GTC          432
Tyr Tyr Ala Lys Gln Lys Ile Thr Val Gly Leu Thr Val Phe Ala Val
    125                 130                 135

GGA AGA TAC ATT GAG CAT TAC TTG GAG GAG TTC TTA ATA TCT GCA AAT          480
Gly Arg Tyr Ile Glu His Tyr Leu Glu Glu Phe Leu Ile Ser Ala Asn
```

```
                                                          -continued 140                 145                 150                 155
ACA TAC TTC ATG GTT GGC CAC AAA GTC ATC TTT TAC ATC ATG GTG GAT         528
Thr Tyr Phe Met Val Gly His Lys Val Ile Phe Tyr Ile Met Val Asp
                    160                 165                 170

GAT ATC TCC AGG ATG CCT TTG ATA GAG CTG GGT CCT CTG CGT TCC TTT         576
Asp Ile Ser Arg Met Pro Leu Ile Glu Leu Gly Pro Leu Arg Ser Phe
            175                 180                 185

AAA GTG TTT GAG ATC AAG TCC GAG AAG AGG TGG CAA GAC ATC AGC ATG         624
Lys Val Phe Glu Ile Lys Ser Glu Lys Arg Trp Gln Asp Ile Ser Met
        190                 195                 200

ATG CGC ATG AAG ACC ATC GGG GAG CAC ATC CTG GCC CAC ATC CAG CAC         672
Met Arg Met Lys Thr Ile Gly Glu His Ile Leu Ala His Ile Gln His
    205                 210                 215

GAG GTG GAC TTC CTC TTC TGC ATG GAC GTG GAT CAG GTC TTC CAA AAC         720
Glu Val Asp Phe Leu Phe Cys Met Asp Val Asp Gln Val Phe Gln Asn
220                 225                 230                 235

AAC TTT GGG GTG GAG ACC CTG GGC CAG TCG GTG GCT CAG CTA CAG GCC         768
Asn Phe Gly Val Glu Thr Leu Gly Gln Ser Val Ala Gln Leu Gln Ala
                240                 245                 250

TGG TGG TAC AAG GCA CAT CCT GAC GAG TTC ACC TAC GAG AGG CGG AAG         816
Trp Trp Tyr Lys Ala His Pro Asp Glu Phe Thr Tyr Glu Arg Arg Lys
            255                 260                 265

GAG TCC GCA GCC TAC ATT CCG TTT GGC CAG GGG GAT TTT TAT TAC CAC         864
Glu Ser Ala Ala Tyr Ile Pro Phe Gly Gln Gly Asp Phe Tyr Tyr His
        270                 275                 280

GCA GCC ATT TTT GGG GGA ACA CCC ACT CAG GTT CTA AAC ATC ACT CAG         912
Ala Ala Ile Phe Gly Gly Thr Pro Thr Gln Val Leu Asn Ile Thr Gln
    285                 290                 295

GAG TGC TTC AAG GGA ATC CTC CAG GAC AAG GAA AAT GAC ATA GAA GCC         960
Glu Cys Phe Lys Gly Ile Leu Gln Asp Lys Glu Asn Asp Ile Glu Ala
300                 305                 310                 315

GAG TGG CAT GAT GAA AGC CAT CTA AAC AAG TAT TTC CTT CTC AAC AAA        1008
Glu Trp His Asp Glu Ser His Leu Asn Lys Tyr Phe Leu Leu Asn Lys
                320                 325                 330

CCC ACT AAA ATC TTA TCC CCA GAA TAC TGC TGG GAT TAT CAT ATA GGC        1056
Pro Thr Lys Ile Leu Ser Pro Glu Tyr Cys Trp Asp Tyr His Ile Gly
            335                 340                 345

ATG TCT GTG GAT ATT AGG ATT GTC AAG ATA GCT TGG CAG AAA AAA GAG        1104
Met Ser Val Asp Ile Arg Ile Val Lys Ile Ala Trp Gln Lys Lys Glu
        350                 355                 360

TAT AAT TTG GTT AGA AAT AAC ATC TGA CTTTAAATTG TGCCAGCAGT              1151
Tyr Asn Leu Val Arg Asn Asn Ile
    365                 370

TTTCTGAATT TGAAAGAGTA TTACTCTGGC TACTTCCTCA GAGAAGTAGC                 1201

ACTTAATTTT AACTTTTAAA AAAATACTAA CAAAATACCA ACACAGTAAG                 1251

TACATATTAT TCTTCCTT                                                    1269

(2) INFORMATION FOR SEQ ID NO:2:

(i) SEQUENCE CHARACTERISTICS:
        (A) LENGTH:18 bases
        (B) TYPE:nucleic acid
        (C) STRANDEDNESS:single
        (D) TOPOLOGY:linear (iii) HYPOTHETICAL:NO (iv) ANTI-SENSE:NO (xi) SEQUENCE DESCRIPTION:SEQ ID NO: 2:
```

```
AAGCTTAAGC TATCGGAC                                                    18
```

(2) INFORMATION FOR SEQ ID NO:3:

(i) SEQUENCE CHARACTERISTICS:
        (A) LENGTH: 18 bases
        (B) TYPE:nucleic acid
        (C) STRANDEDNESS:single
        (D) TOPOLOGY:linear (iii) HYPOTHETICAL:NO (iv) ANTI-SENSE:YES (xi) SEQUENCE DESCRIPTION:SEQ ID NO: 3:

```
CTTAATATCC GCAGGTAG                                                    18
```

(2) INFORMATION FOR SEQ ID NO:4:

(i) SEQUENCE CHARACTERISTICS:
        (A) LENGTH: 20 bases
        (B) TYPE:nucleic acid
        (C) STRANDEDNESS:single
        (D) TOPOLOGY:linear (iii) HYPOTHETICAL:NO (iv) ANTI-SENSE:NO (xi) SEQUENCE DESCRIPTION:SEQ ID NO: 4:

```
CGCTCTAGAA CTAGTGGATC                                                  20
```

(2) INFORMATION FOR SEQ ID NO:5:

(i) SEQUENCE CHARACTERISTICS:
        (A) LENGTH: 18 bases
        (B) TYPE:nucleic acid
        (C) STRANDEDNESS:single
        (D) TOPOLOGY:linear (iii) HYPOTHETICAL:NO (iv) ANTI-SENSE:YES (xi) SEQUENCE DESCRIPTION:SEQ ID NO: 5:

```
CAAAGAACCT TCTGGGCT                                                    18
```

(2) INFORMATION FOR SEQ ID NO:6:

(i) SEQUENCE CHARACTERISTICS:
        (A) LENGTH: 18 bases
        (B) TYPE:nucleic acid
        (C) STRANDEDNESS:single
        (D) TOPOLOGY:linear (iii) HYPOTHETICAL:NO (iv) ANTI-SENSE:NO (xi) SEQUENCE DESCRIPTION:SEQ ID NO: 6:

```
GGCTGGTGGT TTCCGAGC                                                    18
```

(2) INFORMATION FOR SEQ ID NO:7:

(i) SEQUENCE CHARACTERISTICS:
        (A) LENGTH: 18 bases
        (B) TYPE:nucleic acid
        (C) STRANDEDNESS:single
        (D) TOPOLOGY:linear (iii) HYPOTHETICAL:NO (iv) ANTI-SENSE:YES (xi) SEQUENCE DESCRIPTION:SEQ ID NO: 7:

CTCCAAGTAA TCGTCAAT                                                   18

(2) INFORMATION FOR SEQ ID NO:8:

(i) SEQUENCE CHARACTERISTICS:
       (A) LENGTH: 18 bases
       (B) TYPE:nucleic acid
       (C) STRANDEDNESS:single
       (D) TOPOLOGY:linear (iii) HYPOTHETICAL:NO (iv) ANTI-SENSE:NO (xi) SEQUENCE DESCRIPTION:SEQ ID NO: 8:

AGGATGCCTT TGATAGAG                                                   18

(2) INFORMATION FOR SEQ ID NO:9:

(i) SEQUENCE CHARACTERISTICS:
       (A) LENGTH: 20 bases
       (B) TYPE:nucleic acid
       (C) STRANDEDNESS:single
       (D) TOPOLOGY:linear (iii) HYPOTHETICAL:NO (iv) ANTI-SENSE:YES (xi) SEQUENCE DESCRIPTION:SEQ ID NO: 9:

GTCTTGCCAC CTCTTCTCGG                                                 20

(2) INFORMATION FOR SEQ ID NO:10:

(i) SEQUENCE CHARACTERISTICS:
       (A) LENGTH: 18 bases
       (B) TYPE:nucleic acid
       (C) STRANDEDNESS:single
       (D) TOPOLOGY:linear (iii) HYPOTHETICAL:NO (iv) ANTI-SENSE:NO (xi) SEQUENCE DESCRIPTION:SEQ ID NO: 10:

TTCCTCTTCT GCATGGAC                                                   18

(2) INFORMATION FOR SEQ ID NO:11:

(i) SEQUENCE CHARACTERISTICS:
       (A) LENGTH: 18 bases
       (B) TYPE:nucleic acid
       (C) STRANDEDNESS:single
       (D) TOPOLOGY:linear (iii) HYPOTHETICAL:NO (iv) ANTI-SENSE:NO (xi) SEQUENCE DESCRIPTION:SEQ ID NO: 11:

GGGGATTTTT ATTACCAC                                                   18

(2) INFORMATION FOR SEQ ID NO:12:

(i) SEQUENCE CHARACTERISTICS:
        (A) LENGTH: 18 bases
        (B) TYPE:nucleic acid
        (C) STRANDEDNESS:single
        (D) TOPOLOGY:linear (iii) HYPOTHETICAL:NO (iv) ANTI-SENSE:NO (xi) SEQUENCE DESCRIPTION:SEQ ID NO: 12:

GATGAAAGCC ATCTAAAC                                                    18

(2) INFORMATION FOR SEQ ID NO:13:

(i) SEQUENCE CHARACTERISTICS:
        (A) LENGTH: 20 bases
        (B) TYPE:nucleic acid
        (C) STRANDEDNESS:single
        (D) TOPOLOGY:linear (iii) HYPOTHETICAL:NO (iv) ANTI-SENSE:YES (xi) SEQUENCE DESCRIPTION:SEQ ID NO: 13:

ACTCTTCCTT TGACATTCAT                                                  20

(2) INFORMATION FOR SEQ ID NO:14:

(i) SEQUENCE CHARACTERISTICS:
        (A) LENGTH: 23 bases
        (B) TYPE:nucleic acid
        (C) STRANDEDNESS:single
        (D) TOPOLOGY:linear (iii) HYPOTHETICAL:NO (iv) ANTI-SENSE:YES (xi) SEQUENCE DESCRIPTION:SEQ ID NO: 14:

AGCAGCATTG ACAGAACCAC TCT                                              23

(2) INFORMATION FOR SEQ ID NO:15:

(i) SEQUENCE CHARACTERISTICS:
        (A) LENGTH: 18 bases
        (B) TYPE:nucleic acid
        (C) STRANDEDNESS:single
        (D) TOPOLOGY:linear (iii) HYPOTHETICAL:NO (iv) ANTI-SENSE:YES (xi) SEQUENCE DESCRIPTION:SEQ ID NO: 15:

ACATTCATTA TTTTCTCC                                                    18

(2) INFORMATION FOR SEQ ID NO:16:

(i) SEQUENCE CHARACTERISTICS:
        (A) LENGTH: 57 bases
        (B) TYPE:nucleic acid
        (C) STRANDEDNESS:single
        (D) TOPOLOGY:linear (iii) HYPOTHETICAL:NO (iv) ANTI-SENSE:YES (xi) SEQUENCE DESCRIPTION:SEQ ID NO: 16:

```
GGCCGCTCTG GTTATGGTCA CCTGATGAGT CCGTGAGGAC GAAACCTCTG GGCGTTT          57
```

(2) INFORMATION FOR SEQ ID NO:17:

(i) SEQUENCE CHARACTERISTICS:
        (A) LENGTH: 36 bases
        (B) TYPE:nucleic acid
        (C) STRANDEDNESS:single
        (D) TOPOLOGY:linear (iii) HYPOTHETICAL:NO (iv) ANTI-SENSE:NO (xi) SEQUENCE DESCRIPTION:SEQ ID NO: 17:

```
CTAGAAACGC CCAGAGGTCG TGACCATAAC CAGAGC                                 36
```

(2) INFORMATION FOR SEQ ID NO:18:

(i) SEQUENCE CHARACTERISTICS:
        (A) LENGTH: 57 bases
        (B) TYPE:nucleic acid
        (C) STRANDEDNESS:single
        (D) TOPOLOGY:linear (iii) HYPOTHETICAL:NO (iv) ANTI-SENSE:YES (xi) SEQUENCE DESCRIPTION:SEQ ID NO: 18:

```
GGCCGCCTCA ATGTATCTTC CCTGATGAGT CCGTGAGGAC GAAACAGCAA AAACCGT          57
```

(2) INFORMATION FOR SEQ ID NO:19:

(i) SEQUENCE CHARACTERISTICS:
        (A) LENGTH: 36 bases
        (B) TYPE:nucleic acid
        (C) STRANDEDNESS:single
        (D) TOPOLOGY:linear (iii) HYPOTHETICAL:NO (iv) ANTI-SENSE:NO (xi) SEQUENCE DESCRIPTION:SEQ ID NO: 19:

```
CTAGACGGTT TTTGCTGTCG AAGATACAT TGAGGC                                  36
```

(2) INFORMATION FOR SEQ ID NO:20:

(i) SEQUENCE CHARACTERISTICS:
        (A) LENGTH: 58 bases
        (B) TYPE:nucleic acid
        (C) STRANDEDNESS:single
        (D) TOPOLOGY:linear (iii) HYPOTHETICAL:NO (iv) ANTI-SENSE:YES (xi) SEQUENCE DESCRIPTION:SEQ ID NO: 20:

```
GGCCGCAAAG GAACGCAGAG CTGATGAGTC CGTGAGGACG AAACCCAGCT CTATCAAT         58
```

(2) INFORMATION FOR SEQ ID NO:21:

(i) SEQUENCE CHARACTERISTICS:
        (A) LENGTH: 37 bases
        (B) TYPE:nucleic acid
        (C) STRANDEDNESS:single
        (D) TOPOLOGY:linear (iii) HYPOTHETICAL:NO (iv) ANTI-SENSE:N0

(xi) SEQUENCE DESCRIPTION:SEQ ID NO: 21:

CTAGATTGAT AGAGCTGGGT CCTCTGCGTT CCTTTGC            37

(2) INFORMATION FOR SEQ ID NO:22:

(i) SEQUENCE CHARACTERISTICS:
        (A) LENGTH: 51 bases
        (B) TYPE:nucleic acid
        (C) STRANDEDNESS:single
        (D) TOPOLOGY:Linear (iii) HYPOTHETICAL:NO (iv) ANTI-SENSE:YES (xi) SEQUENCE DESCRIPTION:SEQ ID NO: 22 :

UCGGUUAUG GUCACCUGAU GAGUCCGUGA GGACGAAACC UCUGGGCGUU U            51

(2) INFORMATION FOR SEQ ID NO:23:

(i) SEQUENCE CHARACTERISTICS:
        (A) LENGTH: 51 bases
        (B) TYPE:nucleic acid
        (C) STRANDEDNESS:single
        (D) TOPOLOGY:linear (iii) HYPOTHETICAL:NO (iv) ANTI-SENSE:YES (xi) SEQUENCE DESCRIPTION:SEQ ID NO: 23 :

CUCAAUGUAU CUUCCCUGAU GAGUCCGUGA GGACGAAACA GCAAAAACCG U            51

(2) INFORMATION FOR SEQ ID NO:24:

(i) SEQUENCE CHARACTERISTICS:
        (A) LENGTH: 51 bases
        (B) TYPE:nucleic acid
        (C) STRANDEDNESS:single
        (D) TOPOLOGY:linear (iii) HYPOTHETICAL:NO (iv) ANTI-SENSE:YES (xi) SEQUENCE DESCRIPTION:SEQ ID NO: 24 :

AAAGGAACGC AGAGCUGAUG AGUCCGUGAG GACGAAACCC AGCUCUAUCA A            51

(2) INFORMATION FOR SEQ ID NO:25:

(i) SEQUENCE CHARACTERISTICS:
        (A) LENGTH: 24 bases
        (B) TYPE:nucleic acid
        (C) STRANDEDNESS:single
        (D) TOPOLOGY:linear (iii) HYPOTHETICAL:NO (iv) ANTI-SENSE:YES (xi) SEQUENCE DESCRIPTION:SEQ ID NO: 25 :

TCCGAGCTGG TTTAACAATG GGTA            24

```
(2) INFORMATION FOR SEQ ID NO:26:

(i) SEQUENCE CHARACTERISTICS:
        (A) LENGTH: 24 bases
        (B) TYPE:nucleic acid
        (C) STRANDEDNESS:single
        (D) TOPOLOGY:linear (iii) HYPOTHETICAL:NO (iv) ANTI-SENSE:YES (xi) SEQUENCE DESCRIPTION:SEQ ID NO: 26 :

TCTTCGTGGT AACTGTGATG CCTA                                              24
```

α(1,3) GALACTOSYLTRANSFERASE NEGATIVE PORCINE CELLS

This application is a continuation of U.S. application Ser. No. 08/716,443, filed Sep. 16, 1996,(now abandoned), which is a U.S. application based under 35 U.S.C. 371 on PCT/US95/03940, filed Mar. 31, 1995 (abandoned) which is a continuation-in-part of application Ser. No. 08/228,933, filed Apr. 13, 1994 now abandoned.

Donor organ shortages have led to hopes that xenotransplantation could serve as an alternative means of organ availability. Swine, particularly mini-swine, are an attractive alternative to non-human primate donors because of potentially greater availability, the reduced risk of zoonotic infections, appropriate size of organs and the reduced social and ethical concerns (Sachs, D. H. et al. 1976. Transplantation 22:559–567; Auchincloss, H. Jr. 1988. Transplantation 46:1–20). However, one of the major barriers to xenotransplantation is the phenomenon described as hyperacute rejection (Busch et al. 1972. Am. J. Pathology 79:31–57; Auchincloss, H. Jr. 1988. Transplantation 46:1–20). This phenomenon describes a very rapid and severe humoral rejection, which leads to destruction of the graft within minutes or hours of the transplant of the donor organ. Hyperacute rejection is apparently mediated by a complex series of events, including activation of the complement systems, activation of blood coagulation proteins, activation of endothelial cells and release of inflammatory proteins (Busch et al. 1972. Am. J. Pathology 79:31–57; Platt, J. L. 1992. ASAIO Journal 38:8–16). There is an accumulating body of information that implicates a group of pre-formed antibodies, the so-called natural antibodies, to be of fundamental importance in the hyperacute rejection seen in grafts between species. Species combinations in which the recipients of grafts have circulating antibodies that can initiate the hyperacute response to the donor species are described as discordant. Pigs and humans are one such discordant species combination.

The hyperacute rejection process is initiated when the natural antibodies of the recipient bind to cells of the donor organ (Platt et al. 1990. Transplantation 50:870–822; Platt et al. 1990. Immunology Today 11:450–456). It has been suggested that porcine N-linked carbohydrates carrying a terminal Galα1-3Galβ1-4GlcNAc structure are the major targets for anti-swine xenoreactive human natural antibodies (Good et al. 1992. Transplantation Proceedings 24:559–562; Sandrin et al. 1993. Proc. Natl. Acad. Sci. USA 90:11391–11395). One major difference between the glycosylation pattern of swine tissues and human tissues is the presence of high levels of a terminal Galα1-3Galβ1-4GlcNAc structure on swine cells and tissues. This structure is expressed at high levels in all lower mammals investigated, but is poorly expressed on cells and tissues of Old World monkeys, apes and humans (catarrhines) (Galili, U. and Swanson, K. 1992. Proc. Natl. Acad. Sci. USA 88:7401–7404; Galili et al. 1987. Proc. Natl. Acad. Sci. USA. 84:1369–1373). A specific transferase, UDP-Gal:Galβ1→4GlcNAc α1→3-galactosyltransferase (EC 2.4.1.151; α(1,3) galactosyltransferase) is responsible for the transfer of a terminal galactose to the terminal galactose residue of N-acetyllactosamine-type carbohydrate chains and lactosaminoglycans according to the reaction:

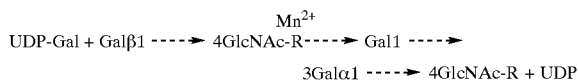

where R may be a glycoprotein or a glycolipid (Blanken, W. M. and Van den Eijinden, D. H. 1985. J. Biol. Chem. 260:12927–12934). Thus the Galα1-3Galβ1-4GlcNAc epitope. Full length CDNA sequences encoding the murine (Larsen et al. 1989. Proc. Natl. Acad. Sci. USA. 86:8227–8231) and bovine (Joziasse et al. 1989. J. Biol. Chem. 264:14290–14297) enzymes have been determined. In addition, the genomic organization of the murine a(1,3) galactosyltransferase gene has been established (Joziasse et al. 1992. J. Biol. Chem. 267:5534–5541). A partial sequence encoding the 3' region of the porcine α(1,3) galactosyltransferase cDNA gene has been determined (Dabkowski et al. 1993. Transplantation Proceedings. 25:2921) but the full length sequence has not been reported. The absence of the 5' sequence is significant for the applications described herein. In contrast to the lower mammals, humans do not express the α(1,3) galactosyltransferase. Furthermore, human sequences homologous to the murine sequence correspond to a processed pseudogene on chromosome 12 and an inactivated remnant on chromosome 9 (Shaper et al. 1992. Genomics 12:613–615).

In accordance with the invention, swine organs or tissues or cells that do not express α(1, 3) galactosyltransferase will not produce carbohydrate moieties containing the distinctive terminal Galα1-3Galβ1-4GlcNAc epitope that is a significant factor in xenogeneic, particularly human, transplant rejection of swine grafts. Further in accordance with the invention, is the aspect of diminishing the production of α(1,3) galactosyltransferase to an extent sufficient to prevent the amount produced from providing carbohydrates with the Galα1-3Galβ1-4GlcNAc epitope from being presented to the cell surface thereby rendering the transgenic animal, organ, tissue, cell or cell culture immunogenically tolerable to the intended recipient without requiring complete α(1,3) galactosyltransferase gene suppression.

One principal aspect of the present invention is that the inventors have isolated the entire porcine α(1,3) galactosyltransferase CDNA gene (SEQ. ID NO. 1). The identification, isolation and sequencing of the entire cDNA gene, now particularly providing the sequence of the 5' end is an important advance because, as described in Example 2, this region has been identified as the most efficient for antisense targeting. Moreover, as compared with mouse and bovine homologous sequences (FIG. 2), this region of the α(1,3) galactosyltransferase MRNA appears to deviate extensively between these species making it extremely unlikely that a use of "cross-species" antisense constructs would be successful.

Another principle aspect of this invention related to genetically altered animals, more specifically transgenic, chimeric or mosaic swine in which the expression of biologically active α(1,3) galactosyltransferase is prevented in at least one organ, tissue or cell type. Transgenic animals carry a gene which has been introduced into the germline of the animal, or an ancestor of the animal, at an early developmental stage. The genetic alteration in transgenic animals is stably incorporated into the genome as a result of intentional experimental intervention. Typically, this results from the addition of exogenous foreign DNA or novel constructs (Palmiter et al. 1986. Ann. Rev. Genet. 20:465). With the advent of embryonic stem (ES) cells and specific gene targeting, the definition of transgenesis now includes specific modification of endogenous gene sequences by direct experimental manipulation and by stable incorporation of DNA that codes for effector molecules that modulate the expression of endogenous genes (Gossler et al. 1986. Proc. Natl. Acad. Sci. USA. 83:9065; Schwarzberg et al. 1989. Science 246:799; Joyner et al. 1989. Nature 338:153).

One preferred approach for generating a transgenic animal involves micro-injection of naked DNA into a cell, preferentially into a pronucleus of an animal at an early embryonic stage (usually the zygote/one-cell stage). DNA injected as described integrates into the native genetic material of the embryo, and will faithfully be replicated together with the chromosomal DNA of the host organism. This allows the transgene to be passed to all cells of the developing organism including the germ line. Transgene DNA that is transmitted to the germ line gives rise to transgenic offspring. If transmitted in a Mendelian fashion, half of the offspring will be transgenic. All transgenic animals derived from one founder animal are referred to as a transgenic line. If the injected transgene DNA integrates into chromosomal DNA at a stage later than the one cell embryo not all cells of the organism will be transgenic, and the animal is referred to as being genetically mosaic. Genetically mosaic animals can be either germ line transmitters or non-transmitters. The general approach of microinjection of heterologous DNA constructs into early embryonic cells is usually restricted to the generation of dominant effects, i.e., one allele of the transgene (hemizygous) causes expression of a phenotype (Palmiter et al. 1986. Ann. Rev. Genetics 20:465.)

In another preferred approach, animals are genetically altered by embryonic stem (ES) cell-mediated transgenesis (Gossler et al. 1986, Proc. Natl. Acad. Sci. USA. 83:9065). ES cell lines are derived from early embryos, either from the inner cell mass (ICM) of a blastocyst (an embryo at a relatively early stage of development) or migrating primordial germ cells (PGC) in the embryonic gonads. They have the potential to be cultured in vitro over many passages (i.e. are conditionally immortalized), and they are pluripotent, or totipotent (i.e. are capable of differentiating and giving rise to all cell types. ES cells can be introduced into a recipient blastocyst which is transferred to the uterus of a foster mother for development to term. A recipient blastocyst injected with ES cells can develop into a chimeric animal, due to the contributions from the host embryo and the embryonic stem cells. ES cells can be transfected with heterologous gene constructions that may cause either dominant effects, inactivate whole genes or introduce subtle changes including point mutations. Subsequent to clonal selection for defined genetic changes, a small number of ES cells can be reintroduced into recipient embryos (blastocysts or morulae) where they potentially differentiate into all tissues of the animal including the germ line and thus, give rise to stable lines of animals with designed genetic modifications. Totipotent porcine embryonic stem cells can be genetically altered to have a heterozygous (+/−) mutant, preferably null mutant allele, particularly one produced by homologous recombination in such embryonic stem cells. Alternatively, gene targeting events by homologous recombination can be carried out at the same locus in two consecutive rounds yielding clones of cells that result in a homozygous (−/−) mutant, preferably a null mutant (Ramirez-Solis et al. 1993. Methods in Enzymol. 225:855).

In one preferred embodiment of this invention a DNA sequence is integrated into the native genetic material of the swine and produces antisense RNA that binds to and prevents the translation of the native MRNA encoding α(1,3) galactosyltransferase in the transgenic swine.

In a particularly preferred embodiment the genome of the transgenic swine is modified to include a construct comprising a DNA complementary to that portion of the α(1,3) galactosyltransferase coding region that will prevent expression of all or part of the biologically active enzyme. As the term is used "integrated antisense sequence" means a nonnative nucleic acid sequence integrated into the genetic material of a cell that is transcribed (constitutively or inducibly) to produce an MRNA that is complementary to and capable of binding with an MRNA produced by the genetic material of the cell so as to regulate or inhibit the expression thereof.

In another embodiment of the invention, cells or cell lines from non-mutant swine are made with the α(1,3) galactosyltransferase inactivated on one or both alleles through the use of an integrated antisense sequence which binds to and prevents the translation of the native MRNA encoding the α(1,3) galactosyltransferase in said cells or cell lines. The integrated antisense sequence, such as the RNA sequence transcribed in Example 3 is delivered to the cells by various means such as electroporation, retroviral transduction or lipofection.

In another preferred embodiment, the transgenic swine is made to produce a ribozyme (catalytic RNA) that cleaves the α(1,3) galactosyltransferase mRNA with specificity. Ribozymes are specific domains of RNA which have enzymatic activity, either acting as an enzyme on other RNA molecules or acting intramolecularly in reactions such as self-splicing or self-cleaving (Long, D. M. and Uhlenbeck, O. C. 1993. FASEB Journal. 7:25–30). Certain ribozymes contain a small structural domain generally of only about 30 nucleotides called a "hammerhead". The hammerhead is a loop of RNA that is flanked by two linear domains that are specific complements to domains on the substrate to be cleaved. The site on the hammerhead ribozyme that effects the cleavage of substrate is the base of the stem loop or hammerhead. As shown in FIG. 3, the ribozymes of the present invention have flanking sequences complementary to domains near the 5'end of the α(1,3) galactosyltransferase cDNA gene.

The DNA for the ribozymes is integrated into the genetic material of an animal, tissue or cell and is transcribed (constitutively or inducibly) to produce a ribozyme which is capable of selectively binding with and cleaving the α(1,3) galactosyltransferase mRNA. As it is a catalytic molecule, each such ribozyme is capable of cleaving multiple substrate molecules.

The catalytic "stem loop" of the ribozyme is flanked by sequences complementary to regions of the α(1,3) galactosyltransferase MRNA. In a particularly preferred embodiment the transgenic swine is modified to integrate a construct comprising the DNA coding for that portion of catalytic RNA necessary to inactivate the mRNA of the α(1,3) galactosyltransferase operably linked to a promoter therefor.

In another embodiment of the invention, cells or cell lines from non-mutant swine are made with the α(1,3) galactosyltransferase inactivated on one or both alleles through the use of an integrated ribozyme sequence which binds to and cleaves the native mRNA encoding the α(1,3) galactosyltransferase in said cells or cell lines. The integrated ribozyme sequence, such as the RNA sequence transcribed in Example 4 is delivered to the cells by various means such as electroporation, retroviral transduction or lipofection.

In another preferred embodiment, using cultured porcine embryonic stem cells, a mutation, preferably a null mutation is introduced by gene targeting at the native genomic locus encoding α(1,3) galactosyltransferase. Gene targeting by homologous recombination in ES cells is performed using constructs containing extensive sequence homology to the native gene, but specific mutations at positions in the gene which are critical for generating a biologically active protein. Therefore, mutations can be located in regions important for either translation, transcription or those coding for functional domains of the protein. Selection for ES clones that have homologously recombined a gene targeting construct, also termed gene "knock out" construct, can be achieved using specific marker genes. The standard procedure is to use a combination of two drug selectable markers including one for positive selection (survival in the presence of drug, if marker is expressed) and one for negative selection (killing in the presence of the drug, if marker is expressed) (Mansour et al., 1988. Nature 336:348) One preferred type of targeting vector includes the neomycin phosphotransferase (neo) gene for positive selection in the drug G418, as well as the Herpes Simplex Virus-thymidine kinase (HSV-tk) gene for selective killing in gancyclovir. Drug selection in G418 and gancyclovir, also termed positive negative selection (PNS) (Mansour et al. 1988. Nature 336:348; Tubulewicz et al. 1991. Cell 65:1153) allows for enrichment of ES cell clones that have undergone gene targeting, rather than random integration events. Confirmation of homologous recombination events is performed using Southern analysis.

The design of the α(1,3) galactosyltransferase targeting construct is described in Example 6. The procedure as applied here uses a positive selection (survival) based on integration of the neo (neomycin resistance), preferably in inverse orientation to the endogenous α(1,3) galactosyltransferase gene locus in a cassette with the phosphoglycerate kinase (PGK-1) promoter and with flanking oligonucleotides complementary to two separate regions of the α(1,3) galactosyltransferase gene sequence. It is understood that other positive selectable markers may be used instead of neo. The neo gene is linked with its promoter to be under control thereof. Downstream from the second flanking sequence is the HSV-tk gene which, if integrated into the genome encodes for production of thymidine kinase making the cell susceptible to killing by gancyclovir (negative selection). The integration of the neo gene but not the HSV-tk gene occurs only where integration into the α(1,3) galactosyltransferase gene has occurred and provides for both positive and negative selection of the cells so transformed.

In another preferred embodiment, using isogenic DNA, it has become possible to achieve high frequency homologous recombination even in biological systems, such as zygotes, which do not lend themselves to the use of elaborate selection protocols and were, therefore, previously not suitable candidates for the isolation of cells which showed positive marker attributes indicating homologous recombination. This use of targeting vectors which include isogenic DNA which is substantially identical to that of chromosomal segments of the target recipient cell, can be used to target zygotes which thereafter develop into transgenic animals. The use of these zygote cells is preferably to produce a mutation, preferably a null mutation, at the chromosomal locus encoding α (1,3) galactosyltransferese. Thus, these vectors contain extensive sequence homology to the native gene, but also contain specific mutations at segments in the gene which are critical for generating a biologically active protein. Therefore, mutations can be located in regions important for either translation, transcription, or those coating for functional domains of the protein. The high percentage of homologous recombination achieved using isogenic DNA makes it possible to avoid the need for selection of clones that have homologously recombined the gene targeting construct, as described above with respect to the "knock out" embodiment thereby making it possible to avoid the need for the standard selection procedure described above.

More particularly, in this embodiment, PCR is used to identify and extract 1–2 kb DNA fragments, which are then subjected to restriction fragment length polymorphism digestions to identify areas or alleles that are most abundantly present in the line of mini-swine selected for zygote injection. Known insertion vectors are used, however, replacement vectors also described in the art could also be used. It is also possible to use DNA sequences with an isogenic replacement vector that require only a few kilobases of uninterrupted isogenic DNA. As such, it is possible to effect highly efficient homologous recombination such that it is not necessary to screen targeting vector recombined zygotes. Rather, genomic DNA screening using PCR can be done after the piglets are born. These transgenic founder animals, which are observed to have the transgene targeted to the native α (1,3) galactosyltransferese locus (i.e. that are heterozygous null mutant for that gene, are grown and interbred to produce animals that are homozygous null mutant for this locus, resulting in the knock out of the α (1,3) galactosyltransferese gene which can be confirmed by antibody or lectin binding assays.

The swine is preferably an α(1,3) galactosyltransferase negative swine grown from a porcine oocyte whose pronuclear material has been removed and into which has been introduced a totipotent porcine embryonic stem cell using protocols for nuclear transfer (Prather et al. 1989, Biol. Reprod. 41:414) ES cells used for nuclear transfer are negative for the expression of α(1,3) galactosyl transferase, or alternatively, totipotent ES cells used for nuclear transfer are mutated in a targeted fashion in at least one allele of the α(1,3) galactosyltransferase gene.

The swine is preferably lacking expression of the α(1,3) galactosyltransferase gene and bred from chimeric animals which were generated from ES cells by blastocyst injection or morula aggregation. ES cells used to generate the preferably null-mutated chimeric animal were mutated at least in one allele of the α(1,3) galactosyltransferase gene locus, using gene targeting by homologous recombination.

A chimeric swine is preferably constituted by ES cells mutated in one allele of the α(1,3) galactosyltransferase gene. Derived from mutated ES cells are also germ cells, male or female gametes that allow the mutation to be passed to offspring, and allow for breeding of heterozygous mutant sibling pigs to yield animals homozygous mutant at the α(1,3) galactosyltransferase locus. Also described is a swine, deficient for an α(1,3) galactosyltransferase protein (i.e., characterized by lack of expression of α(1,3) galactosyltransferase protein) and have little, if any, functional Galα1-3Galβ1-4GlcNAc epitope-containing carbohydrate antigen on the cell surface are produced. Further described are methods of producing transgenic swine and methods of producing tissue from heterozygous swine or homozygous swine of the present invention. The present invention also relates to cell lines, such as swine cell lines, in which the α(1,3) galactosyltransferase gene is inactivated on one or both alleles and use of such cell lines as a source of tissue and cells for transplantation.

Tissues, organs and purified or substantially pure cells obtained from transgenic swine, more specifically from hemizygous, heterozygous or homozygous mutant animals of the present invention can be used for xenogeneic transplantation into other mammals including humans in which tissues, organs or cells are needed. The α(1,3) galactosyltransferase inactive cells can themselves be the treatment or therapeutic/clinical product. For example, keratinocytes rendered α(1,3) galactosyltransferase inactive can be used for macular degeneration and pancreatic cells rendered α(1,3) galactosyltransferase deficient can be used to replace or restore pancreatic products and functions to a recipient. In another embodiment, α(1,3) galactosyltransferase inactive cells produced by the present method are further manipulated, using known methods, to introduce a gene or genes of interest, which encode(s) a product(s), such as a therapeutic product, to be provided to a recipient. In this embodiment, the α(1,3) galactosyltransferase deficient tissue, organ or cells serve as a delivery vehicle for the encoded product (s). For example, α(1,3) galactosyltransferase deficient cells, such as fibroblasts or endothelial cells, can be transfected with a gene encoding a therapeutic product, such as cytokines that augment donor tissue engraftment, Factor VIII, Factor IX, erythropoietin, insulin, human major histocompatibility (MHC) molecules or growth hormone, and introduced into an individual in need of the encoded product.

Alternatively, recipient blastocysts are injected or morulae are aggregated with totipotent embryonic stem cells yielding chimeric swine containing at least one allele of a mutated, preferably null-mutated α(1,3) galactosyltransferase gene produced by homologous recombination. A chimeric swine is preferably constituted by ES cells mutated in one allele of the α(1,3) galactosyltransferase gene. Derived from mutated ES cells are also germ cells that allow the mutation to be passed to offspring, and breeding of heterozygous mutant sibling pigs to yield animals homozygous mutant at the α(1,3) galactosyltransferase locus. Also described is a swine, deficient for an α(1,3) galactosyltransferase protein (i.e., characterized by essentially no expression of α(1,3) galactosyltransferase protein) and with little, if any, functional Galα1-3Galβ1-4GlcNAc epitope-containing carbohydrate antigen on the cell surface are produced. Further described are methods of producing transgenic swine and methods of producing tissue from heterozygous swine or homozygous swine of the present invention. The present invention also related to cell lines, such as swine cell lines, in which the α(1,3) galactosyltransferase gene is inactivated on one or both alleles and use of such cell lines as a source of tissue, organs and cells for transplantation.

FIG. 1 illustrates the complete CDNA sequence of the α(1,3) galactosyltransferase gene (SEQ. ID. No. 1), having an open reading frame of 1113 base pairs, encoding a 371 amino acid protein.

FIG. 2 compares the protein sequences encoded by the porcine, bovine and murine α(1,3) galactosyltransferase cDNA genes.

FIG. 3 illustrates the secondary structure of a transacting hammerhead ribozyme targeted to α(1,3) galactosyltransferase mRNA.

FIG. 4 illustrates the genomic organization of the murine α(1,3-) galactosyltransferase gene. Exons are labeled 1–9 and are indicated by solid boxes. Intron sequences are represented by a thin line.

A method of producing a chimeric swine and porcine organs and tissue cultures, homozygous for an α(1,3) galactosyltransferase gene inactivation, in which α(1,3) galactosyltransferase protein sythesis and cell surface Galα1-3Galβ1-4GlcNAc epitope-containing carbohydrate cell surface markers expression a re deficient is disclosed. Of particular interest are purified cell types which have been rendered deficient in α(1,3) galactosyltransferase expression. Such cell types include fibroblasts, keratinocytes, myoblasts and endothelial cells.

In one embodiment of the present invention, swine cells altered as described herein are used to provide cells needed by a recipient or to provide gene therapy. The cells, which are deficient in Galα(1-3)Galβ1-4GlcNAc epitope-containing carbohydrates cell surface antigen, are cultured and transplanted to an oocyte.

The embryonic stem cells with the null mutant α(1,3) galactosyltransferase locus are introduced into swine blastocysts, which are then introduced into a pseudopregnant swine. The embryo develops into a chimeric swine offspring. When bred with wild-type females, chimeric males transmit the α(1,3) galactosyltransferase inactivation in the embryonic stem cell to their offspring, which are heterozygous for the inactivation. Swine heterozygous for the α(1,3) galactosyltransferase gene inactivation can be intercrossed to produce swine homozygous (−/−) for the mutation.

Purified or substantially pure α(1,3) galactosyltransferase deficient cells can be obtained from tissues or transgenic or chimeric swine produced as described herein. Alternatively, they can be obtained from a normal (non-altered) donor swine and altered using a method described herein. These cells can be then cultured by known methods to produce a quantity of cells useful for transplantation. In addition, cell lines, such as swine cell lines, in which the α(1,3) galactosyltransferase gene is disrupted, preferably on both alleles, are useful as a source of tissue and cells for transplantation.

EXAMPLE 1

Isolation and Characterization of Porcine α(1,3) Galactosyltransferase cDNA

A previously described λZAP II porcine spleen cDNA library (Gustafsson et al. 1990. Proc. Natl. Acad. Sci. USA. 87:9798–9802) was screened by hybridization with a cloned α(1,3) galactosyltransferase cDNA probe (Joziasse et al. 1989. J. Biol. Chem. 264:14290–14297) The Genbank Accession number for the bovine α(1,3) galactosyltransferase CDNA sequence is J04989. The bovine a(1,3) galactosyltransferase cDNA probe was kindly provided by Dr. David Joziasse, University of Leiden, The Netherlands. The probe was radioactively labeled with a $^{32}$P-DATP using the Megaprime DNA labeling system (Amersham International, UK). Positive clones were confirmed by the polymerase chain reaction (PCR), using primers (SEQ. ID. NO: 2 and SEQ. ID. NO: 3) derived from the bovine α(1,3) galactosyltransferase cDNA sequence. SEQ. ID. NO: 2 corresponds to bovine α(1,3) galactosyltransferase nucleotides 712–729 and SEQ. ID. NO: 3 corresponds to the reverse complement of bovine α(1,3) galactosyltransferase nucleotides 1501–1508. Recombinant pBluescript plasmids from positive clones were automatically excised with the helper phage R408 (Stratagene Ltd., Cambridge, UK) and amplified in *E. coli* strain TGl (ATCC 39078). Plasmid DNA was prepared using the Magic Miniprep kit (Promega Ltd., Southampton, UK) following the manufacturer's instructions and the DNA was characterized by cleavage with EcoRI. DNA sequencing was performed by the dideoxy chain termination method, using a T7 DNA polymerase sequencing kit Pharmacia Biosystems Ltd., Milton Keynes, UK) according to the manufacturer's instructions. The synthetic oligonucleotide primers SEQ. ID. NOs. 4–12 were used. SEQ. ID. NO. 4 is Stratagene SK, catalog number 300305, (Stratagene Inc., La Jolla, Calif. ). SEQ. ID. NO: 5 corresponds to the reverse complement of porcine α(1,3) galactosyltransferase nucleotides 94–111. SEQ. ID. NO: 6 corresponds to the porcine α(1,3) galactosyltransferase nucleotides 163–180. SEQ. ID. NO: 7 corresponds to the reverse complement of porcine α(1,3) galactosyltransferase nucleotides 442–459. SEQ. ID. NO: 8 corresponds to the complement of porcine and bovine α(1,3) galactosyltransferase nucleotides 538–555 and 982–999, respectively. SEQ. ID. NO: 9 corresponds to the reverse complement of porcine α(1,3) galactosyltransferase nucleotides 596–615. SEQ. ID. NO: 10 corresponds to the porcine α(1,3) galactosyltransferase nucleotides 682–699. SEQ. ID. NO: 11 corresponds to the porcine α(1,3) galactosyltransferase nucleotides 847–864. SEQ. ID. NO: 12 corresponds to the reverse complement of porcine α(1,3) galactosyltransferase nucleotides 970–987.

Four positive clones were obtained from approximately 2×10[4] plaques screened by hybridization with the bovine α(1,3) galactosyltransferase CDNA probe (Joziasse et al. 1989. J. Biol. Chem. 264:14290–14297). Three of these clones were confirmed to be positive by PCR. Each of the three recombinant pBluescript plasmids, generated by automatic excision from λZapII with helper phage, contained inserts of approximately 2.5 kb as determined by EcoRI cleavage. One clone, designated pSα13GTI, was selected for further study.

DNA sequence analysis of pSα13GT1 revealed an open reading frame of 1113 bases (See SEQ. ID. NO: 1 and FIG. 1) showing 86% identity with the published bovine cDNA sequence (Joziasse et al. 1989. J. Biol. Chem. 264:14290–14297) and encoding a 371 amino acid protein with 85% and 76% identity with the bovine and murine α(1,3) galactosyltransferase amino acid sequences, respectively (FIG. 2).

EXAMPLE 2

Antisome Oligonucleotide Inhabition of α(1,3) Galactosyltransferase Expression Three antisense 5' and 3' phosphothioate-protected oligonucleotides (S-oligonucleotides, SEQ. ID. NOs 13–15) are tested in an in vitro system employing porcine primary endothelial cell cultures (from porcine aorta) and a porcine B-cell line (L231, European Collection of Animal Cell Cultures, PHLS, Center for Applied Microbiology and Research, Porton Down, Salisbury, UK). SEQ. ID. NO: 13 corresponds to the reverse complement of porcine α(1,3) galactosyltransferase cDNA nucleotides 16–35. SEQ. ID. NO: 14 corresponds to the reverse complement of porcine α(1,3) galactosyltransferase CDNA nucleotides 31–53. SEQ. ID. NO: 15 corresponds to the reverse complement of porcine α(1,3) galactosyltransferase cDNA nucleotides 6–23. All three antisense oligonucleotides are directed at the 5' region of the mRNA surrounding the initiation of translation. Nonsense S-oligonucleotides randomized from the antisense sequence are used as controls at similar molar concentrations.

Porcine endothelial cells are derived from miniature swine aorta by scraping the luminal surface of the blood vessel as described (Ryan et al. Tissue and Cell 12:619–635). The cells are suspended in M199 medium supplemented with 20% fetal bovine serum (GIBCO BRL, Gaithersburg, Md.) and gentamycin and plated in 25 ct$^2$ tissue culture flasks, pre-coated with fibronectin (5 μg/cm$^2$) and laminin (1 μg/cm$^2$). Endothelial cell growth supplement (Collaborative Research, Bedford, Mass.) at 150 μg/ml is added at the beginning of the culture. The cultures are maintained by changing one half of the medium every 2–3 days. The porcine lymphoblastoid cell line L231 is maintained in DMEM, 10% fetal bovine serum, 10% NCTC-109, 1% glutamine, 1% pen-strep (all from GIBCO BRL, Gaithersburg, Md.) and 5×10–$^2$ M 2-mercaptoethanol (Sigma, St. Louis, Mo.). The L231 cells are sub-cultured by splitting the cells 1:3 every three days.

For cell treatment, S-oligonucleotides are added, to a final concentration of 5–10 μM, to growing cells at 24 hr intervals, typically for 48 hr, and then the treated cells are examined for the levels of α(1,3) galactosyltransferase mRNA (by Northern blot analysis) and expression of the epitope on the cell surface by human AB serum and FITC-labeled mouse anti-human secondary reagents (anti-human IgM and IgG).

EXAMPLE 3

Preparation and use of Integrated Antisense Constructs

We are studying the ability of integrated antisense constructs to inhibit specifically the production of the porcine α(1,3) galactosyltransferase. Specific inhibition of the α(1,3) galactosyltransferase in transfected cells allows assessment of the contribution of the enzyme in the hyperacute phenomenon. Vectors are constructed to express the α(1,3) galactosyltransferase antisense MRNA, under the control of the cytomegalovirus (CKV) promoter. Specifically, pSα13GT1 is cleaved with NotI and EcoRV which generates a restriction fragment of length 537 bp, containing part of the pBluescript polylinker sequence through to nucleotide 531 of the α(1,3) galactosyltransferase cDNA sequence. This DNA fragment is cloned into the expression vector pcDNA3 (Invitrogen, San Diego, Calif.), cleaved with the same enzymes. The resulting vector therefore contains the porcine α(1,3) galactosyltransferase sequence in the antisense direction, relative to the CKV promoter located in pcDNA3. The construct is transfected, using electroporation or other high efficiency methods for introducing DNA into mammalian cells, into both porcine endothelial cells and the L231 porcine lymphoblastoid cell lines (grown as described in Example 2). The effect of the antisense RNA is monitored by both Northern blot analysis of mRNA of the α(1,3) galactosyltransferase gene and the degree of binding of human serum components (i.e., natural antibodies).

EXAMPLE 4

Ribozyme Sequences that Inactivate Porcine α(1,3) Galactosyltransferase mRNA This example describes a method for construction of the vectors which encode ribozyme sequences which are specifically designed to cleave the porcine α(1,3) galactosyltransferase mRNA sequence.

The design of the ribozyme sequences is based upon the consensus cis-acting hammerhead ribozyme sequence (Ruffner et al. 1990. Biochemistry 29:10695–10702). we used the Zuker algorithm in the suite of programs available from the Genetics Computer Group (Madison, Wis.) to model the cis-acting hammerhead ribozyme sequences (Denman, R. B. 1993. BioTechniques 15:1090–1095). Ribozyme target sequences are identified within the α(1,3) galactosyltransferase mRNA sequence. A ribozyme sequence file for each potential ribozyme sequence is generated based on the target sequence and using five nucleotides to connect the MRNA target sequence with the catalytic strand of the ribozyme. The sequence file is then folded into the lowest energy structure using RNAFOLD. Sequences which have non-ribozyme structures are discarded. FIG. 3 illustrates one of the ribozyme-target RNA secondary structures, using the ribozyme corresponding to SEQ. ID. NO. 16. The small arrow indicates the cleavage site on the mRNA, between stem I and stem III.

Synthetic oligonucleotides to encode the ribozymes (SEQ. ID. NOs. 16–21) are made on an Applied BioSystems Oligonucleotide synthesizer (Foster City, Calif.) with termini corresponding to the overhangs of the restriction endonucleases NotI and XbaI. The duplex DNA is cloned into the mammalian expression cloning vector pcDNA3 (Invitrogen, Calif.). Expression of the ribozyme is under the control of the CMv promoter present in pcDNA3. The transcripts consist of approximately 140 nucleotides both 5' and 3' to the ribozyme sequence. The expression level of the transcribed sequence is ascertained by Northern blot analysis. If the RNA level is low additional sequences will be included in the construct in order to generate a longer and more stable transcript.

The construct is transfected using the electroporation technique into porcine primary endothelial cells, porcine B cells (L231). Also, the vector is co-transfected with plasmid expressing the porcine $\alpha(1,3)$ galactosyltransferase into COS7 cells. Since COS7 cells do not express an endogenous $\alpha(1,3)$ galactosyltransferase, the effect of the presence of the ribozyme on the expression of the introduced porcine $\alpha(1,3)$ galactosyltransferase gene is easily ascertained.

EXAMPLE 5

Transgenic Swine Producing Antisense or Ribozyme RNA that Inhabit $\alpha(1,3)$ Galactosyltransferase Sybtessis This approach requires direct microinjection of transgene DNA into one of the pronuclei of a porcine embryo at the zygote stage (one-cell embryo). Injected one-cell embryos are transferred to recipient foster gilts for development to term (Hammer et al. 1985, Nature 315:680; Pursel et al. 1989, Science 244:1281)

Critical to successfully accomplishing this approach is the age and weight of the donor pigs, preferentially the haplotype specific mini-swine. Optimally, the animals are of age 8 to 10 months and weigh 70 to 85 lbs. This increases the probability of obtaining adequate supply of one-cell embryos for microinjection of the transgenes. In order to allow for accurate timing of the embryo collections at that stage from a number of embryo donors, the gilts are synchronized using a preparation of synthetic progesterone ,3 (Regumate). Hormone implants are applied to designated gilts 30 days prior to the date of embryo collection. Twenty days later, ten days prior to the date of collection, the implants are removed and the animals are treated with additional hormones to induce superovulation i.e. to increase the number of embryos for microinjection. Three days following implant removal, the animals are treated with 400 to 1000 IU of pregnant mare serum gonadotropin (PMSG) and with 750 IU of human chorionic gonadotropin (hCG) three to four days later. These animals are bred by artificial insemination (AI) on two consecutive days following injection of hCG.

Embryo collections are performed as follows: three days following the initial injection of hCG, the animals are anesthetized with an intramuscular injection of Telazol (3 mg/lb.), Rompum (2 mg/lb.) and Atropine (1 mg/lb.). A midline laparotomy is performed and the reproductive tract exteriorized. Collection of the zygotes is performed by cannulating the ampulla of the oviduct and flushing the oviduct with 10 to 15 ml phosphate buffered saline, prewarmed to 39° C. Following the collection, the donor animals are prepared for recovery from surgery according to USDA guidelines. Animals used twice for embryo collections are euthanized according to USDA guidelines.

Injection of the transgene DNA into the pronuclei of the zygotes is carried out as follows. Zygotes are maintained in HAM's F-12 medium supplemented with 10% fetal calf serum at 38° C. in 5% $CO_2$ atmosphere. For injection the zygotes are placed into modified BMOC-2 medium containing HEPES salts (Ebert et al. 1984. J. Embryol. Exp. Morph. 84:91–103), centrifuged at 13,000×g to partition the embryonic lipids and visualize the pronuclei. The embryos are placed in an injection chamber (depression slide) containing the same medium overlaid with light paraffin oil. Microinjection is performed on a Nikon Diaphot inverted-microscope equipped with Nomarski optics and Narishige micro-manipulators. Using 40× lens power the embryos are held in place with a holding pipette and injected with a glass needle which is back-filled with the solution of DNA containing the transgene (2 $\mu$g/ml). Injection of approximately 2 picoliters of the solution (4 femptograms of DNA) which is equivalent to around 500 copies of the transgene is monitored by the swelling of the pronucleus by about 50%. Embryos that are injected are placed into the incubator prior to transfer to recipient animals.

Recipient animals are prepared similar to the donor animals, but not superovulated. Prior to the transfer of the injected embryos, recipient gilts are anesthetized, the abdomen opened surgically by applying a longitudinal incision and the ovaries exteriorized. The oviduct ipsilateral to the ovary with the larger number of corpus lutei is flushed, the embryos checked to evaluate if the animals is reproductively sound. Approximately 4 to 6 zygotes injected with the transgene are transferred to the flushed oviduct, the abdominal incision sutured and the animals placed in a warm area for recovery. The status of the pregnancy is monitored by ultrasound starting at day 25, or approximately one week following the expected date of implantation. Pregnant recipients are housed separately until they are due to farrow.

Newborn piglets are analyzed for integration of the transgene into chromosomal DNA. Genomic DNA is extracted from an ear punch or a blood sample and initial screening is performed using PCR. Animals that are potentially transgene-positive are confirmed by Southern analysis. Transgenic founder animals are subjected to further analysis including the levels of expression, phenotype and germ line transmission. Northern analysis from RNA of selective tissues including endothelial cells is performed to determine the level of transgene expression. Also, immunological assays including flow cytometric analysis for binding of antibody from human serum and complement mediated lysis of pig cells recognized by human natural antibodies are carried out to evaluate the transgene effect. Animals that satisfy the above criteria are used as founders for breeding of a transgenic line. If the founder transgenic animals only satisfy part of the requirements, breeding and specific inter-crossing of transgenic offspring is performed to assay the transgene effect in homozygous animals.

EXAMPLE 6

A Swine Made Null-Mutant for $\alpha(1.3)$ Galactosyltransferase by Homologous Recombination Using Porcine Embryonic Stem Cells Gene targeting by homologous recombination in swine requires several components, including the following: (A) a mutant gene targeting construct including the positive/negative drug-selectable marker genes (Tubulewicz et al. 1991. Cell 65:1153); (B) embryonic stem cell cultures; and (C) the experimental embryology to reconstitute an animal from the cultured cells.

The targeting construct is provided from a genomic clone that spans most of the $\alpha(1,3)$ galactosyltransferase gene and is isolated from a library made of isogenic DNA from a major histocompatibility complex (MHC) haplotype d/d of the miniature swine. Fragments of that genomic clone are introduced into a positive/negative selectable marker cassette specifically developed for gene targeting in embryonic stem (ES) cells and termed PPNT (Tubulewicz et al. 1991. Cell 65:1153). This gene targeting cassette includes as positive selectable marker the bacterial neomycin phosphotransferase gene (neo) which allows for selection of cells in G418. The neo gene is regulated by a promoter that guarantees high level expression in ES cells such as the phosphoglycerate kinase promoter-1 (PGK-1). Negative selection is accomplished by expressing the Herpes Simplex Virus—thymidine kinase (HSV-tk) gene which allows for selective killing of cells in Gancyclovir. Similar to the neo gene, the HSV-tk gene is regulated by the PGK-1 promoter, as well. In the targeting cassette pPNT there are unique and convenient cloning sites between the neo and the HSV-tk gene which are suitable sites to introduce the genomic fragment of the $\alpha(1,3)$ galactosyltransferase gene upstream of the translation initiation signal AUG (e.g. SalI sites in introns 2 and 4) This fragment of approximately 2 kb of DNA is cloned in reverse orientation to the direction of transcription of the PGK-neo cassette to assure that no truncated or residual peptide is generated at the $\alpha(1,3)$ galactosyltransferase-locus. Genomic sequences of the $\alpha(1,3)$ galactosyltransferase locus downstream of exon 4, approximately 5 kb are introduced into pPNT at the 5'-end of the neo gene. This targeting construction termed pPNT-alpha GT1 is linearized and transfected by electroporation into porcine ES cells. Double selection in G418 (150 to 300 $\mu$g/ml) and Gancyclovir is performed to initially isolate clones of ES cells with targeted mutations in the $\alpha(1,3)$ galactosyltransferase locus. Confirmation of homologous recombinant clones is achieved using Southern analysis.

ES cell clones that have undergone targeted mutagenesis of one allele of the $\alpha(1,3)$ galactosyltransferase locus are subjected to a second round of in vitro mutagenesis or used for reconstituting an animal that contains the mutation. A second round of in vitro mutagenesis can be carried out using an analogous targeting construction with hygromycin phosphotransferase hyg as positive selectable marker gene.

As far as the reconstitution of animals is concerned, the methods include nuclear transfer, blastocyst injection or morula aggregation. The preferred routes include either blastocyst injection or morula aggregation which yield chimeras between the donor cells and the recipient embryos. For both these methods recipient embryos are prepared as follows: embryo donor/recipient gilts are synchronized and mated as described in Example S. On day 6 following artificial insemination or natural mating, the gilts are prepared for surgery as described earlier, anesthetized and the uteri retrogradely flushed using a prewarmed (38° C.) solution of phosphate buffered saline (PBS). Intact blastocysts that are encapsulated by the zona pellucida are placed in a depression slide containing HEPES-buf fered medium (whitten's or TL-HEPES) and approximately 15 to 20 ES cells are injected into the blastocoel using a glass injection needle with an opening of 20 $\mu$m and Narishige micromanipulators. Injected embryos are then reimplanted into recipient foster gilts for development to term and pregnancies are monitored using ultrasound. Offspring is analyzed for chimerism using the polymerase chain reaction (PCR) of DNA samples extracted from blood, skin and tissue biopsies and primers complementary to the neo or hyg gene. Germ line transmission of the chimeras is assayed using PCR and in situ hybridization of tissue samples obtain from male and female gonads. Male and female chimeras which transmit the ES cell genotype to the germ line are crossed to yield homozygously mutant animals. Analysis of mutant animals for expression of $\alpha(1,3)$ galactosyltransferase and binding of human natural antibodies to endothelial cells of those animals is used as final test to assess the validity of gene knock out approach in swine.

EXAMPLE 7

A Swine Made Null-Mutant for $\alpha(1,3)$ Galactosyltransferase Using Isogenic DNA Targeting Into Zygotes Isogenic DNA or DNA that is substantially identical in sequence between the targeting vector and target DNA in the chromosomes greatly increases the frequency for homologous recombination events and thus the gene targeting efficiency. Using isogenic DNA-targeting vectors, targeting frequencies of 80% or higher are achieved in mouse embryonic stem cells. In contrast, non-isogenic DNA-vectors normally yield targeting frequencies of around 0.5% to 5%, i.e., approximately two orders of magnitude lower than isogenic DNA vectors. Surprisingly, isogenic DNA constructions are predominantly integrated into chromosomes by homologous recombination rather than random integration. As a consequence, targeted mutagenesis of genes can, therefore, be carried out in biological systems, including animals and even zygotes, which do not lend themselves to the use of elaborate selection protocols.

The significance for isogenic DNA in gene targeting approaches was first described by TeRiele et al., PNAS 89, 5128–5132 (1992) and also in PCT/US 92/07184.

In order for the isogenic DNA approach to be feasible, targeting vectors have to be constructed from a source of DNA that is identical to the DNA of the organism to be targeted. Ideally, isogenic DNA targeting is carried out in inbred strains of animals in which all genetic loci are homozygous. All animals of that strain can therefore serve as a source for generating isogenic targeting vectors. In cases in which inbred strains of animals are lacking, genetic loci can consist of many different alleles. Thus, isogenic vectors can only be derived from the individual in which targeted gene replacement is attempted. Furthermore, the targeting vector would be isogenic for one allele only.

In the haplotype specific miniature swine, isogenic gene targeting vectors are readily derived for the MHC locus, since that genomic region has been maintained homozygous for several generations. Since the CDNA sequence to $\alpha(1,3)$ galactosyltransferase locus has been determined (Example 1) and genomic clones have been generated recently it is now possible to map and thereby avoid, polymorphisms within the $\alpha(1,3)$ galactosyltransferase locus gene.

Mapping of polymorphism is carried out as follows. A group of mini-swine that are closely related, either siblings and/or parent/offspring is identified. High molecular weight DNA is extracted and PCR reactions are set up to amplify sequences from Exon 6 to Exon 7 spanning Intron 6. The organization of Exons 5 through 9 of the porcine gene are known to be homologous to those of the murine gene (FIG. 4, Joziasse, D. H., Shaper, N. L., Kim, D., Van den Eijnden, D. and Joel H. Shaper, J. Biol. Chem. 167, pp. 5534–5541 (1992)). In FIG. 4, genomic organization of the murine $\alpha(1,3-)$ galactosyltransferase gene Exons are labeled 1–9 and are indicated by solid boxes. Intron sequences are represented by a thin line. The 5'-oligo in Exon 6 has the following sequence: 5'- TCC GAG CTG GTT TAA CAA TGG GTA -3' (SEQ ID NO: 25) and the 3' oligo in Exon 7 contains the following sequence: 5'- TCT TCG TGG TAA CTG TGA GTC CTA -3' (SEQ ID NO: 26). The PCR fragments are approximately 1 and 2 kb long. In order to assay for PCR-RFLPs, restriction digestions using 4-cutters are carried out which are expected to cut frequently. Such 4-cutters include BstU I (CGCG), Hae III (GGCC), Hha I (GCGC) Sau3A (GATC), Rsa I (GTAC) and Taq I (TCGA), which are commercially available from New England BioLabs (Beverley, Mass.). Based on the pattern of restriction fragments obtained from parental animals and offspring, as well as between siblings, it is possible to define the number of different alleles present in that group of animals. In case the PCR-RFLP does not yield obvious sequence polymorphisms between different alleles in different animals, alternative methods can be employed including DNA sequencing or enzyme mismatch cleavage (EMC) using T7 or T4 resolvases. Additional animals are then analyzed in a similar manner to identify specific alleles at the $\alpha 1,3$ galactosyltransferase locus. Once several alleles have been identified, targeting constructions are prepared for those alleles that are most abundantly present in the line of mini-swine selected for zygote injection.

Gene targeting constructions are generated as follows. A genomic library is made in lambda replacement vectors including Lambda FIX II, Lambda EMBL4 or Lambda Dash II (Stratagene Cloning Systems). The library is then plated at a density of around 50,000 plaques/15 cm plate and screened with a probe specific for Exon 9 of the swine $\alpha(1\ 3)$ galactosyltransferase gene. The probe is generated using PCR which is carried out using a standard protocol: 35 cycles, anneal at 60° C. for 20 sec, extend at 72° C. for 40 sec and denature at 94° C. for 20 sec. Positive clones with insert sizes of around 15 kb are then subcloned into plasmid vectors including pSP72 and engineered for targeting as either an insertion vector or a replacement vector.

An insertion vector is designed as described by Hasty and Bradley (Gene Targeting Vectors for Mammalian Cells, in Gene Targeting: A Practical Approach, ed, Alexandra L. Joyner, IRL Press 1993). Insertion vectors require for only one crossover to occur for integration by homologous recombination into the native locus. The double strand breaks, the two ends of the vector which are known to be highly recombinogenic, are located on adjacent sequences on the chromosome. Preferably the site of integration of the insertion vector is at the beginning of Intron 8 of the $\alpha(1,3)$ galactosyltransferase gene. The entire length of Intron 8 is thereby included as a homologous and identical sequence, carrying the minimal number mismatches. Exon 9 which encodes the catalytic domain of the enzyme is then substituted by a selectable marker such as the neomycin phosphotransferase gene, or a derivative thereof termed IRES 6geo. Downstream, or 3' of the selectable marker, sequences from Intron 7, Exon 8 and Intron 8 are included, terminating at the site adjacent to the beginning of the vector. The targeting frequencies of that construction are in the range of 30 to 50%. All these constructions are made using standard cloning procedures.

The replacement vectors have also been extensively described by Hasty and Bradley, supra. Conceptually more straightforward than the insertion vector, replacement vectors issued here are essentially co-linear fragments of a certain stretch of genomic sequence at the $\alpha(1,3)$ galactosyltransferase locus. Preferably, the DNA sequence from which an isogenic replacement vector is constructed include approximately 6 to 10 kb of uninterrupted DNA. This DNA corresponds to a region between the start of Exon 4 and the end of Intron 8 of certain alleles of the a (1,3) galactosyltransferase locus from mini-swine. Exon 9, encoding the catalytic domain is replaced with the selectable marker gene, such as the neo gene, or a functional analog thereof. The 3'-end of the replacement vector includes the 3' untranslated region of the gene in Exon 9, including approximately 1 kb of isogenic DNA. Two crossovers, one on either side of the selectable marker causes the mutant targeting vector to become integrated and replace the wild-type gene.

Microinjection of the isogenic transgene DNA into one of the pronuclei of a porcine embryo at the zygote stage (one-cell embryo), particularly the mini-swine, is accomplished by modification of the protocol described earlier. (Hammer et al. 1985, Nature 315, 680; Pursel et al 1989, Science 244, 1281). Optimally, the mini-swine are of age 8 to 10 months and weigh 70 to 85 lbs. This increases the probability of obtaining an adequate supply of one-cell embryo donors. The gilts are synchronized using a preparation of synthetic progesterone (Regumate). Hormone implants are applied to designated gilts 30 days prior to the date of embryo collection. Twenty days later, ten days prior to the date of collection, the implants are removed and the animals are treated with additional hormones to induce superovulation, i.e., to increase the number of embryos for microinjection. Three days following implant removal, the animals are treated with 400 to 1000 IU of pregnant mare serum gonadotropin (PMSG) and with 750 IU of human chorionic gonadotropin (hCG) three to four days later. These animals are bred by artificial insemination (AI) on two consecutive days following injection of hCG.

Embryo collections are performed as follows. Three days following the initial injection of hCG, the animals are anesthetized with an intramuscular injection of Telazol (3 mg/lb), Rompum (2 mg/lb) and Atropine (1 mg/lb). A midline laparotomy is performed and the reproductive tract exteriorized. Collection of the zygotes is performed by cannulating the ampulla of the oviduct and flushing the oviduct with 10 to 15 ml phosphate buffered saline, pre-warmed to 39° C. Following the collection, the donor animals are prepared for recovery from surgery according to USDA guidelines. Animals used twice for embryo collections are euthanized according to USDA guidelines.

Injection of the transgene DNA into the pronuclei of the zygotes is carried out as summarized below. Zygotes are maintained in HAM F-12 medium supplemented with 10% fetal calf serum at 38° C. in 5% $CO_2$ atmosphere. For injection the zygotes are placed into BMOC-2 medium, centrifuged at 13,000 g to partition the embryonic lipids and visualize the pronuclei. The embryos are placed in an injection chamber (depression slide) containing the same medium overlaid with light paraffin oil. Microinjection is performed on a Nikon Diaphot inverted-microscope equipped with Nomarski optics and Narishige micromanipulators. Using 40× lens power the embryos are held in place with a holding pipette and injected with a glass needle which is back-filled with the solution of DNA containing the transgene (2 $\mu$g/ml). Injection of approximately 2 picoliters of the solution (4 femptograms of DNA) which is equivalent to around 500 copies of the transgene is monitored by the swelling of the pronucleus by about 50%. Embryos that are injected are placed into the incubator prior to transfer to recipient animals.

Recipient animals are prepared similar to the donor animals, but not superovulated. Prior to the transfer of the injected embryos, recipient gilts are anesthetized, the abdomen opened surgically by applying a longitudinal incision and the ovaries exteriorized. The oviduct ipsilateral to the ovary with the larger number of corpus lutei is flushed and the embryos are checked to evaluate if the animal is reproductively sound. Approximately 4 to 6 zygotes injected with the transgene are transferred to the flushed oviduct, the abdominal incision sutured and the animals placed in a warm area for recovery. The status of the pregnancy is monitored by ultrasound starting at day 25, or approximately one week following the expected date of implantation. Pregnant recipients are housed separately until they are due to farrow.

Newborn piglets are analyzed for integration of the transgene into chromosomal DNA. Genomic DNA is extracted from an ear punch or a blood sample and initial screening is performed using PCR. Animals that are potentially transgene-positive are confirmed by Southern analysis. Transgenic founder animals are subjected to further analysis regarding the locus of transgene integration using Southern analysis. Those animals that have the transgene targeted to the native α(1,3) galactosyltransferase locus, i.e., that are heterozygous mutant for that gene, are grown up and bred to additional heterozygous mutant founder animals. Applying Mendelian genetics allows us to breed animals that are homozygous mutant for the α(1,3) galactosyltransferase. Functional assays using the lectin B14 and human preformed natural antibodies are then used to look at expression of the Gal α(1,3) Gal epitope on swine cells and to confirm the knockout of the α(1,3) galactosyltransferase gene.

What is claimed is:

1. A product, comprising: isolated porcine cells in which the normal expression of œ (1,3) galactosyltransferase is inhibited, said cells including a galactosyltransferase gene encoding a polypeptide comprising the amino acid sequence of SEQ. ID NO: 1, wherein said gene has been disrupted to inhibit normal expression of œ(1,3) galactosyltransferase.

2. The product of claim 1 wherein said gene includes an inactivating mutation produced by homologous recombination with DNA isogenic to said gene, said DNA including a mutation that inactivates said gene to prevent normal expression of œ(1,3) galactosyltransferase.

3. The product of claim 1 wherein the product comprises swine tissue.

4. A process for producing isolated porcine cells that normally do not express galactosyltransferase, comprising: disrupting in isolated porcine cells a galactosyltransferase gene encoding a polypeptide comprising the sequence of SEQ ID NO: 1 by homologous recombination with DNA isogenic to said gene, said isogenic DNA including a mutation that disrupts said gene to prevent normal expression of galactosyltransferase.

* * * * *

UNITED STATES PATENT AND TRADEMARK OFFICE
CERTIFICATE OF CORRECTION

PATENT NO. : 6,413,769 B1
DATED : July 2, 2002
INVENTOR(S) : Baetscher et al.

It is certified that error appears in the above-identified patent and that said Letters Patent is hereby corrected as shown below:

Column 31,
Line 21, change "oe" to -- $\alpha$ --.
Line 25, change "oe" to -- $\alpha$ --.
Line 30, change "oe" to -- $\alpha$ --.

Signed and Sealed this

Twenty-ninth Day of October, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,413,769 B1
DATED : July 2, 2002
INVENTOR(S) : Gustafsson et al.

It is certified that error appears in the above-identified patent and that said Letters Patent is hereby corrected as shown below:

Title page,
Item [73], Assignee, after "(US)", add -- ; Biotransplant, Inc., Medford, MA (US) --.

Column 31,
Lines 21, 25 and 30, change "oe" to -- α --.

Signed and Sealed this

Eighteenth Day of May, 2004

JON W. DUDAS
*Acting Director of the United States Patent and Trademark Office*